United States Patent [19]
Yost et al.

[11] Patent Number: 5,827,951
[45] Date of Patent: Oct. 27, 1998

[54] SOLDERABILITY TEST SYSTEM

[75] Inventors: Fred Yost, Cedar Crest; Floyd M. Hosking; James L. Jellison, both of Albuquerque, all of N. Mex.; Bruce Short; Terri Giversen, both of Beverly, Mass.; Jimmy R. Reed, Austin, Tex.

[73] Assignee: Sandia National Laboratories, Albuquerque, N. Mex.

[21] Appl. No.: 426,543

[22] Filed: Apr. 21, 1995

[51] Int. Cl.⁶ .................................................. G01N 13/00
[52] U.S. Cl. .......................... 73/53.01; 73/64.48; 228/103
[58] Field of Search ................ 73/53.01, 61.41, 73/61.43, 61.62, 64.48, 64.52, 866; 228/103

[56] References Cited

U.S. PATENT DOCUMENTS 4,467,638  8/1984  Greenstein .............................. 73/64.4
4,529,116  7/1985  Gutbier ................................... 228/103

Primary Examiner—Michael Brock

[57] ABSTRACT

A new test method to quantify capillary flow solderability on a printed wiring board surface finish. The test is based on solder flow from a pad onto narrow strips or lines. A test procedure and video image analysis technique were developed for conducting the test and evaluating the data. Feasibility tests revealed that the wetted distance was sensitive to the ratio of pad radius to line width (l/r), solder volume, and flux predry time.

18 Claims, 10 Drawing Sheets

2

SOLDERABILITY TEST SYSTEM

The government has rights in this invention pursuant to Contract No. DE-AC04-76DP00789 awarded by the U.S. Department of Energy.

BACKGROUND OF THE INVENTION

This invention relates to a system and method for predicting the solderability of metallizations on printed wiring boards. More specifically, the invention relates to the relationship of the radius of a circular metallized solder pad at one end to the width of a contiguous metallized strip extending therefrom in terms of solder flow onto the strip from the pad as a technique to provide a standardized solderability test for use in surface mount technology electronics packages.

Industry studies estimate that 30% of a printed wiring board (PWB) defects are related to soldering, and one third of those defects are related to insufficient wetting. Existing solder wettability tests (dip and look, wetting balance, area-of-spread, meniscus rise, rotary dip, globule, etc.) are neither fully understood nor uniformly accepted. One reason is a noticeable lack of reproducibility of results. None of these techniques simulate the capillary flow physics of surface mount technology (SMT) soldering processes. Such processes involve solder flow along metallized surfaces and into the gap between surface mount devices and printed wiring boards. The present invention measures such flow and serves as a valuable soldering index for typical microelectronic geometries and is particularly suitable for SMT applications. The invention is also useful in the control of solder flow on a PWB by varying the conductor geometry. By reducing the line width to the critical dimension defined by the ratio of the line width to solder pad radius, solder flow can be restricted to the contact pad without the application of solder resist/mask. This final benefit has a significant impact on controlling solder placement while maintaining excellent solder wettability at the solder joint.

SUMMARY OF THE INVENTION

A solderability test vehicle (TV) having a lollipop-shaped metallization with a pad of radius r and a conductor line of width d and length X extending therefrom is used to predict solder flow from the pad onto the line as a function of the ratio of d:r. (Note: in the following discussing the dimension "d" is also referred to as "δ" or "l") The solderability of the line can be predicted by measuring the flow rate of the solder onto the line from the pad and also by the final length of the solder as it extends out onto the line. Also, the flow of the solder on to the line from the pad can be prevented by reducing the width of the line below a certain critical ratio of d:r which is dependent on the equilibrium contact angle of the solder and the size of the wetting hysterisis band. This "no flow" condition is a useful alternative to the employment of solder resist/mask to prevent such flow.

DETAILED DESCRIPTION OF THE INVENTION

Figure 1:
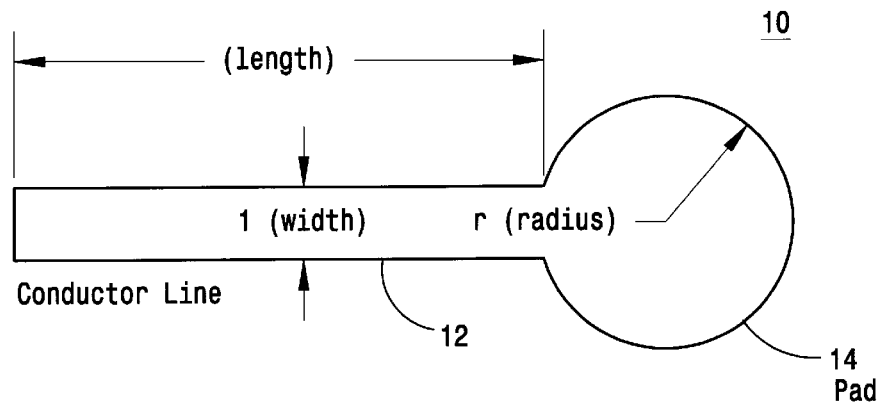
FIG. 1 is a diagram showing the dimensions and nomenclature for the test vehicle.

This new capillary flow technique provides a soldering index for evaluating most microelectronics geometries. It can be directly applied to the control of solder flow on a printed wiring board (PWB). Solder flow can be restricted by adjusting the line width to pad radius ratio. This ability to predict capillary flow has the potential to improve significantly solder placement and wetting The individual lollipop metallizations 10 are emplaced on a PWB substrate with conventional metallization techniques, here copper was used. Common to the capillary flow test vehicle's geometry is a metal strip 12 extending from a circular base pad 14 as shown in FIG. 1. Consider the circular metallization pattern having radius, $r_c$, and let a small volume of solder wet and spread to a radius $r<r_c$, such that capillary equilibrium occurs at a contact angle, $\theta_c$. Let the solder volume be increased to a value $V_o$, just large enough to allow the solder to spread to the metallization radius. Any further increase of volume will increase the contact angle to a value $\theta_{+c}>\theta_c$, but will not increase the radius since the wettable metallization extends only as far as $r_c$. In this quadrajunction configuration, there exists an excess pressure that would drive solder flow if more metallization were available. Consider the additional metallization of a very slender rectangular strip of width $\delta<r_c$ connected to the circular pad. The excess pressure would move solder onto the strip for certain values of the ratio $\delta$ to $r_c$. Solder would flow a distance, x, reducing the pressure over the circular metallization until it equals that above the strip. To simplify the flow or spreading calculations, it is assumed that the test geometry is small enough to neglect the effect of gravity on solder shape. Thus, the solder on the circular metallization would have a spherical cross section, while the solder on the strip would be circular. After solder flows onto the strip, an equilibrium contact angle, $\theta_c$, is established on the circular metallization. Although the molten solder dissolves and reacts with the substrate, the change of solder volume during this process is negligible. The pattern can be fabricated with different pad radii, line widths, and line lengths by either etching or depositing additional metal layers. Either single-sided substrates or doubled coupons with specified gaps can be used to simulate various capillary flow conditions. Theoretical analysis suggests that a line width to pad radius ratio (d/r) of 0.5 or greater is necessary for solder to flow onto the strip. A more detailed mathematical treatment of this process is to be found at the end of this Detailed Description. The test procedure and preliminary experimental results are presented below.

Materials and Capillary Flow Test Procedure

The capillary flow test vehicle (CFTV) used in this study was fabricated using conventional PWB materials and fabrication technologies. The CFTV demonstration substrate, 0.060" thick, was an epoxy resin laminate reinforced with glass fiber cloth (FR-4). Copper patterns (0.5 oz.) were printed and etched per the specified "lollipop" test geometry. Additional copper was electrodeposited on the vendor Cu to a final conductor thickness of 35 µm (1 oz. Cu). Ninety one snap-out test specimens were available per test panel. Powder-free finger cots or latex gloves were used when handling individual specimens to minimize contamination from oils, greases, salts, or other foreign debris. Transporting of CFTVs was done with stainless steel tweezers by gripping along the CFTV edge.

Figure 2:
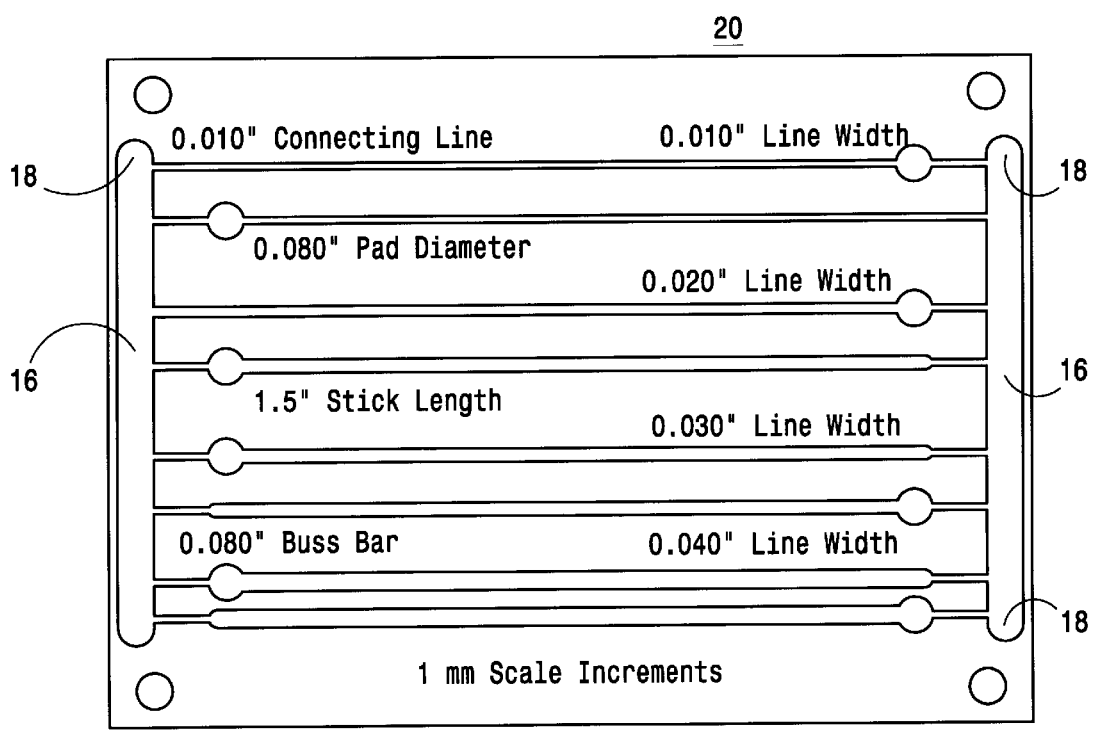
FIG. 2 is a top view of the capillary flow test vehicle, CFTV2.

The CFTV design has evolved into the version, 20, shown in FIG. 2. The substrate has duplicate test patterns with line width-to-pad radius ratios (d/r) of 0.25, 0.5, 0.75, and 1.0. The pad radius was held constant at 0.040", with line widths ranging from 0.010 to 0.040". The line length (or maximum possible capillary flow) was 1.5". One millimeter (1.0 mm) reference marks were also patterned onto the TVs and were used as calibration or datum points during video image analysis of the floated coupons. Buss bars 16 and connecting conductive lines 18 between test patterns were also incorporated into the TV design for depositing other surface finishes (e.g., Ni, Sn, and Au). Free surface spread tests were conducted with a single CFTV. Restricted capillary flow between controlled gaps can be evaluated by stacking two TVs together ("doubled" TVs) and maintaining a constant gap with corner shims.

Soldermask and organic solderability preservative (OSP) are other PWB surface features that can be applied to the CFTV. Three CFTV sets having a Cu surface finish with a benzotriazole-based OSP coating were fabricated for initial testing. The sets differed only in the application of soldermask (none, 0.001" or 0.003" thick). Soldermask was applied by liquid photo imaging (0.001") or with dry film photoresist (0.003"). The board vendor applied the OSP coating before shipping to retain solder wettability during subsequent storage and handling.

Preliminary CFTV wetting experiments were conducted with eutectic Sn—Pb (63Sn-37Pb, wt. %) solder paste and pellets. The paste consisted of 85% solder and the balance rosin mildly activated (RMA) flux and carrier. RMA liquid flux and solder pellets were also applied to the CFTV before testing. The liquid flux was diluted 1:1 with isopropyl alcohol yielding a nominal 25% solids flux. The CFTV samples were cleaned before solder floating per the following procedure. Baseline samples were degreased in trichloroethylene, followed by a rinse in isopropyl alcohol. The substrates were then cleaned in a 10% HCl and deionized water solution for 3 minutes to remove the vendor applied OSP, rinsed in hot tap water, rinsed in deionized water, rinsed in isopropyl alcohol, and finally blown dry with technical grade nitrogen gas. Since most commercial precleaners are based on proprietary chemistries that are routinely changed, precleaning standardization is very important. The above technique provides a consistent method for preparing uniform Cu test surfaces.

Test specimens were coated with flux following the precleaning step. TVs were gently agitated in a flux bath for 5 to 10 seconds. After slow withdrawal from the flux, the TVs were held vertically for approximately 15 seconds and blotted along their bottom edges to remove excess flux. After fluxing and draining, solder pellets or paste were placed on each TV pad 14 per the following procedure: (a) solder pellets of known weight were dipped in flux and placed immediately on the fluxed CFTV pads or (b) solder paste was applied to the fluxed CFTVs with a dispensing gun; the dispensed paste was accurately measured (±0.1 mg) by taring out the TV's pre-weight on an analytical balance and then weighing the TV after applying the solder paste.

CFTV preheating was not done during preliminary testing, since typical reflow soldering equipment was not available and reproducing a reflow profile was not possible. A flux predry was not considered during initial CFTV testing. As tests were conducted, however, a hold period before solder floating was found to significantly improve test consistency by vaporizing the alcohol carrier of the flux. The effects of flux drying will be discussed below in more detail.

CFTV tests were conducted by floating samples on a standard thermostatically controlled solder pot. The total surface area of the solder bath was sufficiently large enough to avoid touching the sides of the solder pot. Test temperatures were maintained within ±2° C. The nominal baseline test temperature was 245° C. CFTVs were initially floated for 60 seconds, and subsequently for longer times (90–120 seconds) to capture the complete wetting event. A minimum of 15–25 seconds typically elapsed before the applied solder melted. Samples were carefully removed from the solder bath after testing to minimize agitation of the molten solder on the TV. This was accomplished by holding the TV in a horizontal position until the solder solidified. Flux residues were then removed by rinsing with trichloroethylene.

Capillary flow data were analyzed from recorded video images. A black and white, charged-couple device (CCD) camera and professional video tape recorder with time code generator were used to record the wetting images. The camera was mounted perpendicular to the floated CFTV. A fiber optic light source was used to illuminate the test surface. Digital image analysis was subsequently conducted with a PC-based image processor. Final wetted distance and flow rate for each line width were measured from selected test images.

Test Results and Observations

Preliminary testing used the general procedures described above. CFTV test panels were fabricated by Alternate Circuit Technology, Ward Hill, Mass. The Cu surface finishes were coated with Entek Cu-56 OSP. Kester Solder, Des Plaines, Ill. fabricated solder pellets ranging in weight from 4 to 18 mg. ESP Solder Plus supplied the solder paste, 85% 63Sn-37Pb solder with 15% RMA flux. The TVs were dipped in Alpha 611 RMA flux, nominally 25% solids. CFTV precleaning was done per the described cleaning procedure. Tests were conducted with both solder pellets and paste. The effects of float temperature and solder volume on capillary flow were investigated. The experimental parameters are listed in Table 1. Tests were performed in random order.

TABLE 1

CFTV Test Parameters

| Temperature (°C.) | Solder Type | Solder Weight (mg) |
|---|---|---|
| 230 | Pellet | 4.0 ± 0.1 |
| 260 | " | " |
| 230 | " | 18.5 ± 0.3 |
| 260 | " | " |
| 245 | " | 10.3 ± 0.1 |
| 230 | Paste* | 4.1 ± 0.1 |
| 260 | " | " |
| 230 | " | 18.1 ± 0.1 |
| 260 | " | " |
| 245 | " | 11.0 ± 0.1 |

*reported weight is net metal weight (85% of applied paste)

Figure 3:
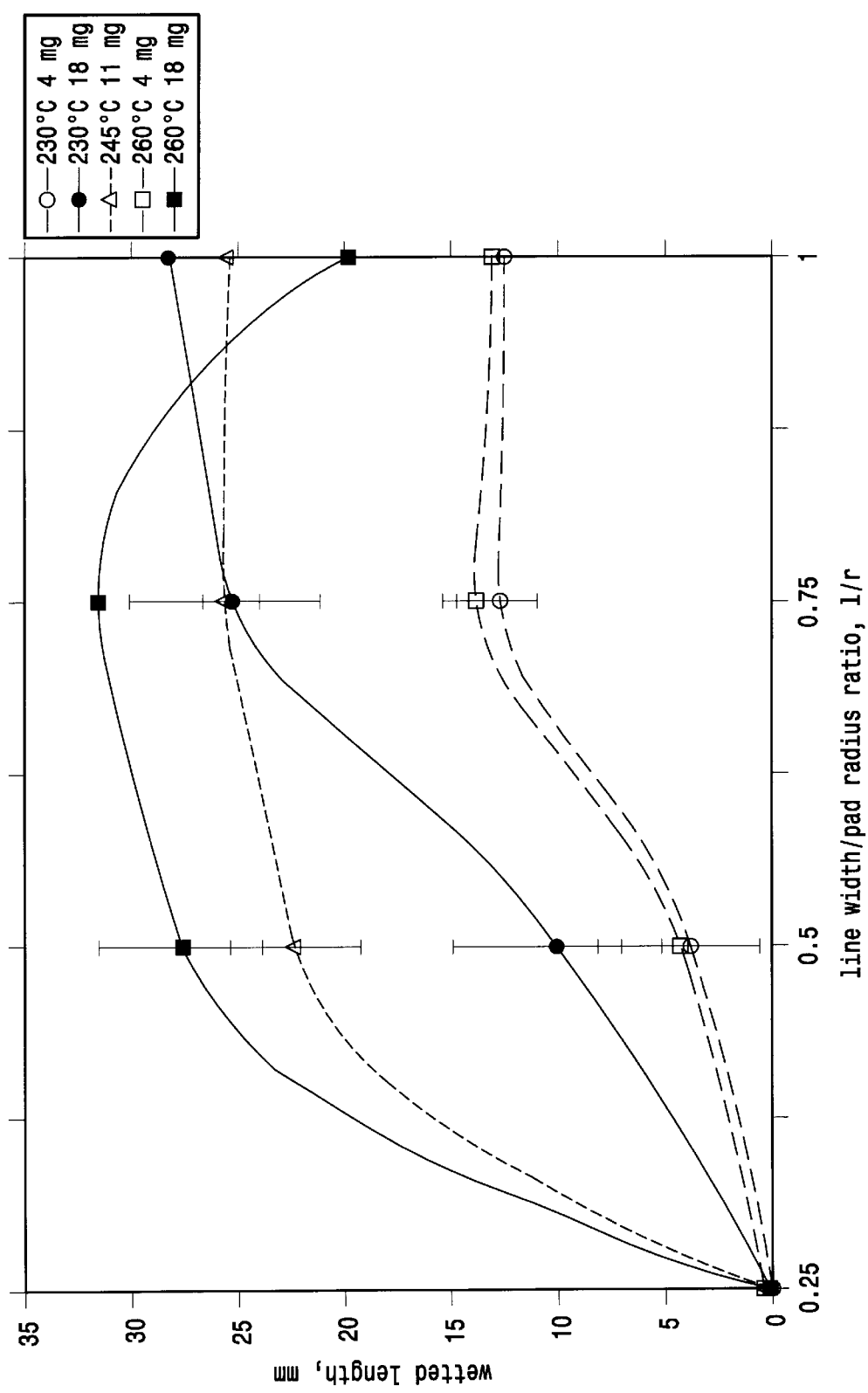
FIG. 3 is a graph showing wetted length as a function of temperature and solder paste weight (net solder) for different line widths (pad radius=0.040").
Figure 4:
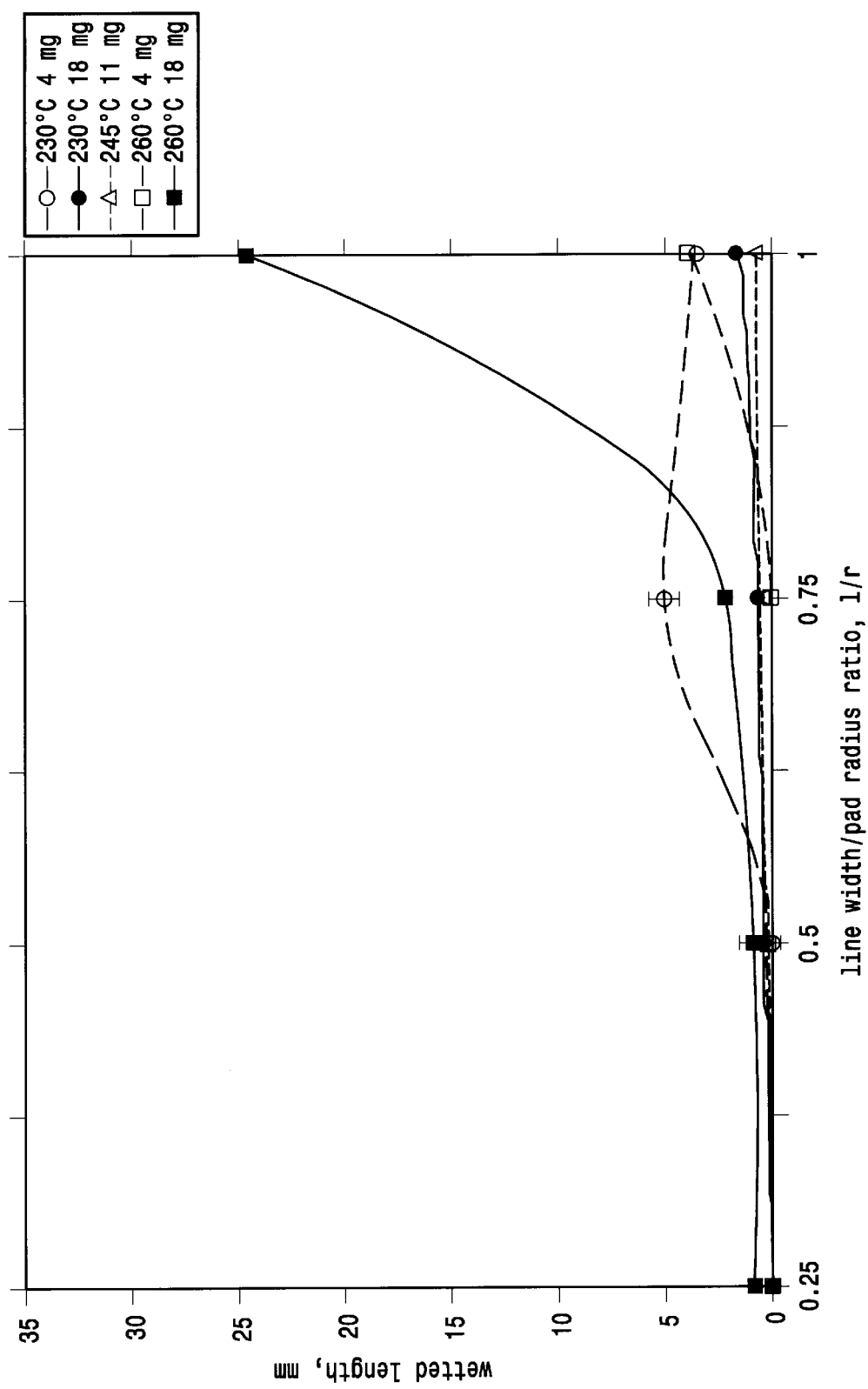
FIG. 4 is a graph showing wetted length as a function of temperature and solder pellet weight for different line widths (pad radius=0.040"). Samples were immediately solder floated after being coated with an RMA flux.

CFTV specimens were fluxed and immediately tested without preheating or predrying. The wetting distance results are summarized in FIGS. 3 & 4 for the solder paste and pellet tests, respectively. The data represents only a limited number of tests, but does provide some insight into the effects of temperature, solder type and volume, and line width on capillary flow. The wetting distance was generally sensitive to solder type. During reflow, the solder paste typically flowed further than the solder pellets. After closer examination of the test results, it was discovered that 20 to 30 minutes elapsed between fluxing and floating of the solder paste CFTV2 specimens compared to the much shorter times of 5 minutes or less with the solder pellet samples. The longer delay before paste testing was the result of the "tare and weigh" procedure used to determine the paste weight on each test pad. The flux carrier from the TV and solder paste volatilizes more effectively with increasing hold times or a preheat. Less flux splatter and reduced evaporative surface cooling would consequently improve wetting. The extended hold time could also accelerate the chemical reaction between the Cu finish and flux.

Figure 5:
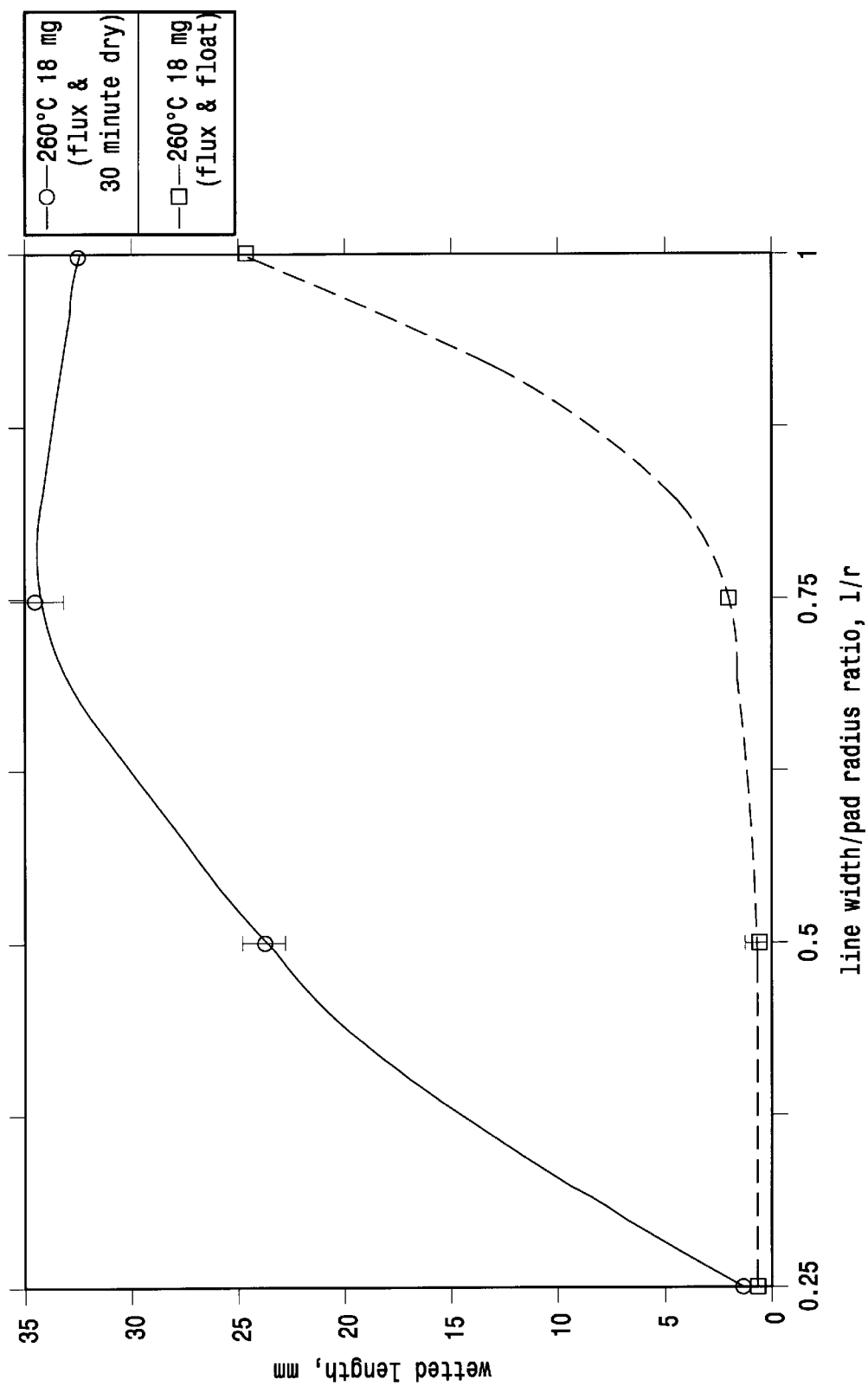
FIG. 5 is a graph showing wetted length as a function of different line widths (pad radius=0.040") for 18 mg solder pellets at 260° C. where the samples were solder floated immediately (bottom curve) or 30 minutes (top curve) after flux application.

To verify the effect of flux drying time on solder wetting and flow, additional experiments were conducted at 260° C. with 18 mg solder pellets and a 30 minute hold after fluxing. The effect of drying on wetting is shown in FIG. 5. It is clear that hold time has a significant effect on capillary flow.

Figure 6:
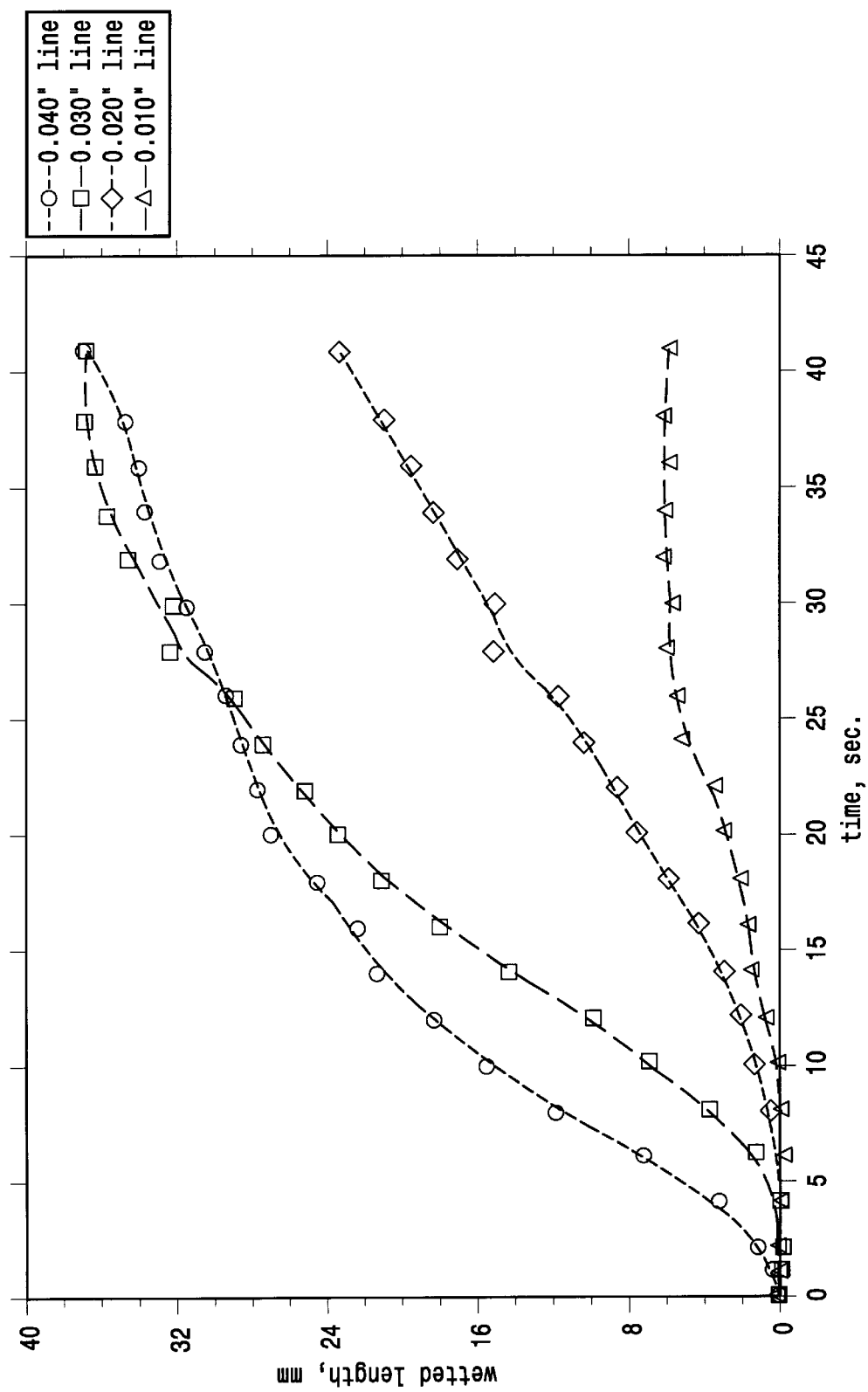
FIG. 6 is a graph showing nominal wetted length after a 30 minute flux predry with 18 mg solder pellets at 245° C. for different line widths (pad radius=0.040").
Figure 7:
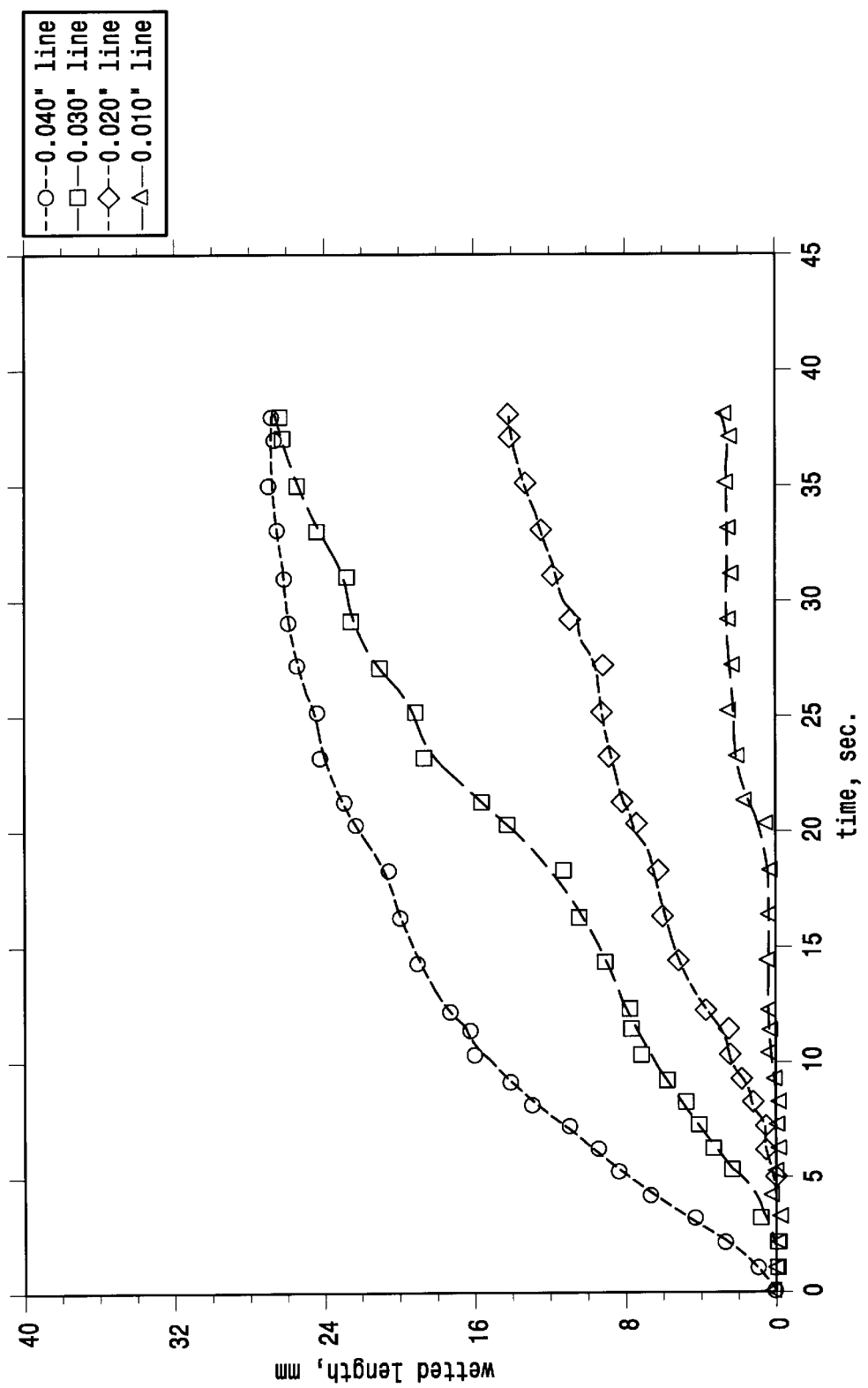
FIG. 7 is a graph showing nominal wetted length after a 30 minute flux predry with 18 mg solder pellets at 260° C. for different line widths (pad radius=0.040").

Preliminary image analyses of videotaped experiments (18 mg solder pellets and RMA flux) confirmed the sensitivity of solder flow to the predry time. Flux coated samples were allowed to dry for 30 minutes before floating at 245° and 260° C. for one minute. The results are summarized in FIGS. 6 and 7. The wetting curves represent the average of both line pattern replicates. The 0.040" line initially wetted faster than the other line widths. The 0.030" line, however, eventually gave similar or better capillary flow, as demonstrated by the 245° C. test. Intermediate wetting rates and lengths were observed and measured on the 0.020" line pattern. The 0.010" pattern yielded negligible capillary flow. The results compare quite favorably with the proposed flow model which predicts capillary flow if the l/r ratio is ≧0.5 (or line widths ≧0.020" with a pad radius of 0.040"). The wetting rates also appear to be greater at 245° C. than at 260° C. Oxidation of the Cu surface at the higher temperature could be competing with the wetting/flow mechanism or the reduced activity of the flux.

The video analyses also revealed a problem in the experimental technique. Individual solder pellets on the CFTV were observed to melt at slightly different times. A cursory evaluation with a thermocoupled TV revealed that temperature variations of up to 10° C. are possible during specimen floatation. These temperature variations could influence capillary flow and test repeatability. Conducting tests with standard reflow equipment should reduce the thermal difference.

Figure 8:
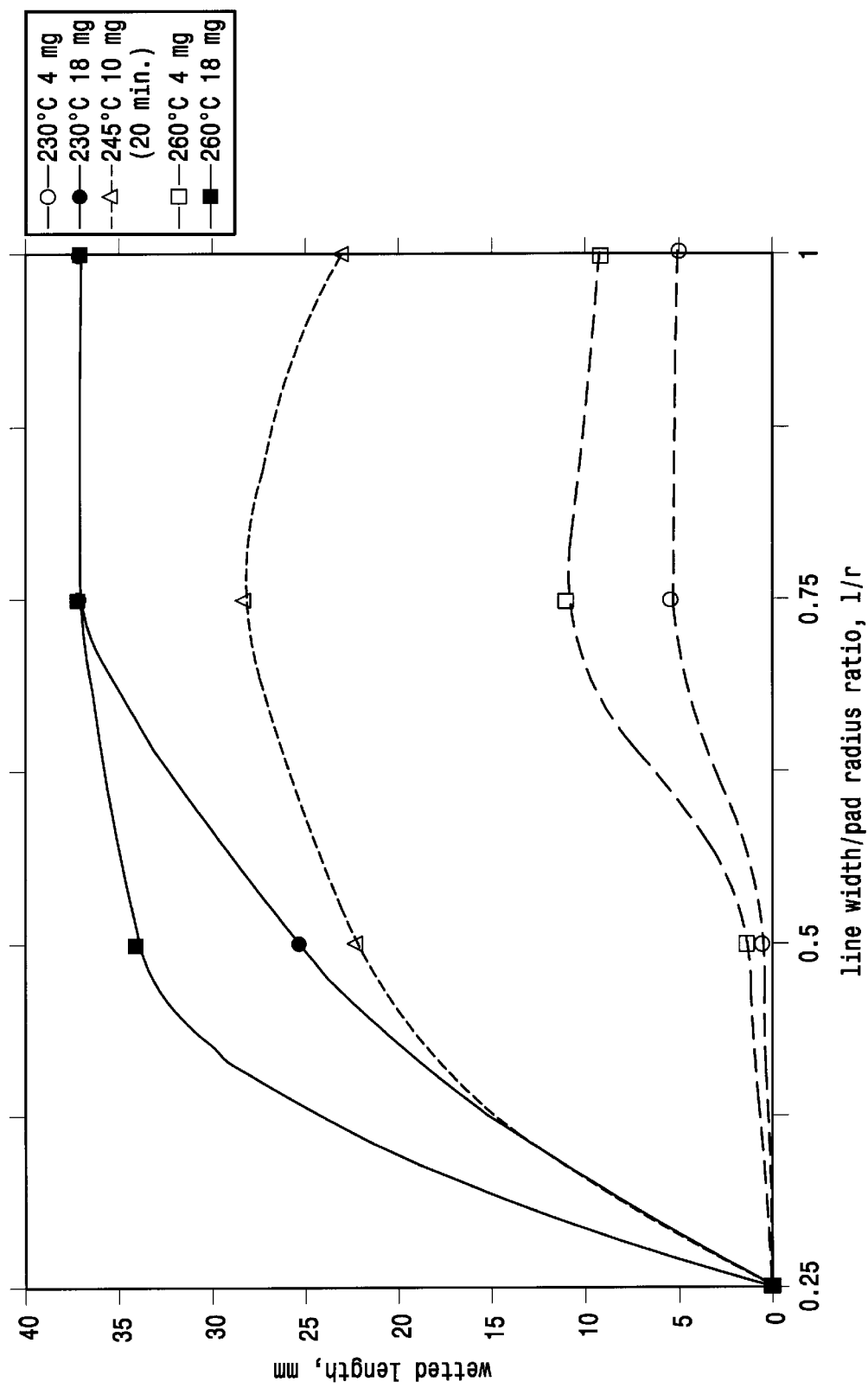
FIG. 8 is a graph showing wetted length as a function of different line widths (pad radius=0.040"), solder pellet weights, and test temperatures with a 10 minute flux predry (twenty minute predry for the 245° C. tests).
Figure 9:
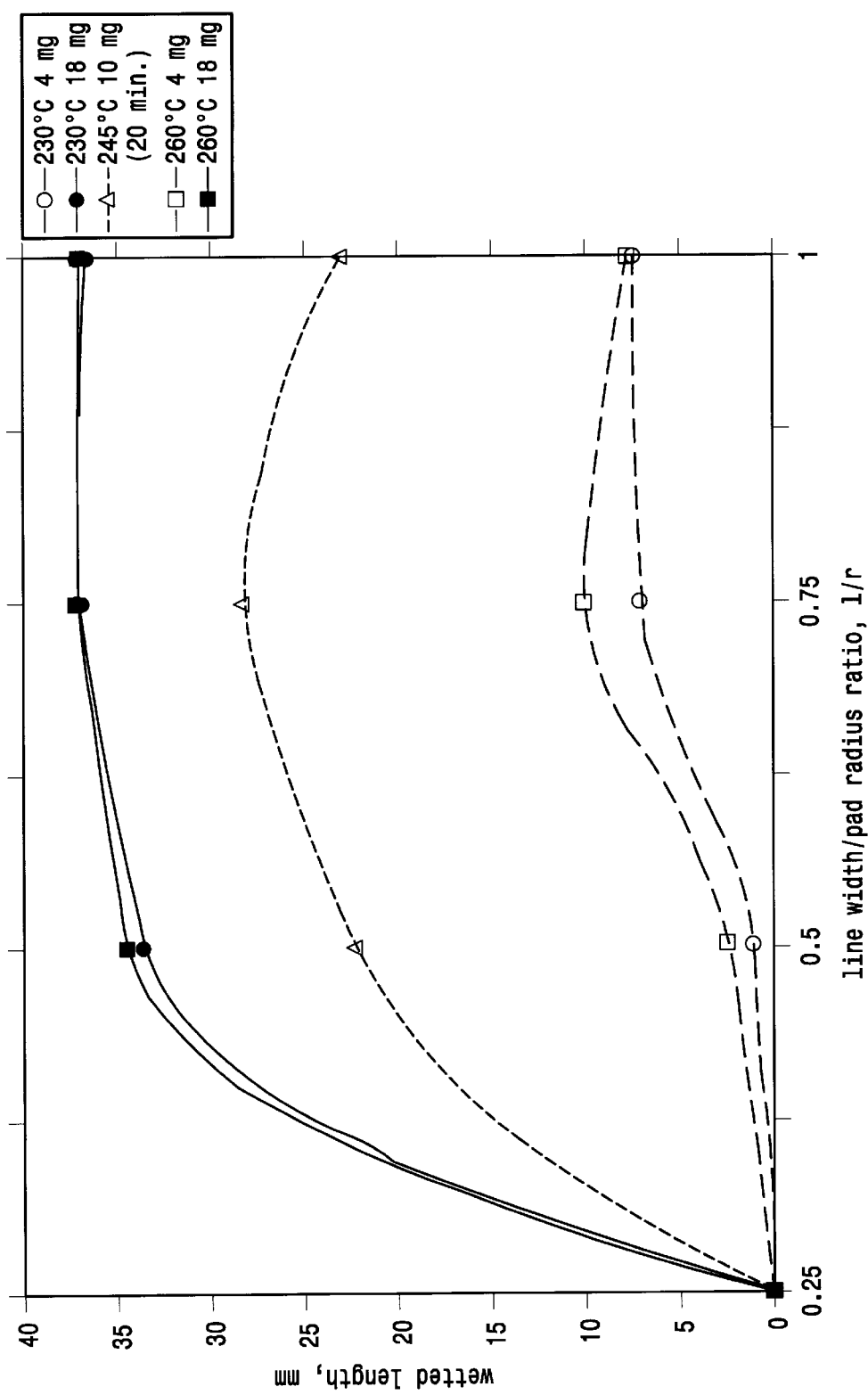
FIG. 9 is a graph showing nominal wetted length as a function of different line widths (pad radius=0.040"), solder pellet weights, and test temperatures with a 30 minute flux predry (twenty minute predry for the 245° C. tests).

Additional experiments were conducted recently to quantify the predry time effects on wetting. FIGS. 8 and 9 summarize the results. The longer 30 minute predry generally normalized the flow data at each solder volume with increasing test temperature. For example, little difference was observed in the individual 4 and 18 mg solder pellet flow curves as the temperature was increased from 230° to 260° C. The maximum wetted distance was primarily affected by the solder volume under these test conditions.

The above results demonstrate the feasibility of the capillary flow solderability test method. The flow results are very sensitive to test and surface conditions. The issues of flux application, CFTV preheating or drying, surface environmental stressing, surface roughness, flow between "doubled" substrates with a controlled gap, and test repeatability are being further investigated. Nevertheless, this invention constitutes the development of a representative test method for determining the solderability of PWBs. The test will be used to evaluate new or modified PWB surface finishes.

Theoretical Analysis

The purpose of this section is to evaluate and model the behavior of a test vehicle that captures certain aspects of capillary behavior. The test vehicle (TV) is a small printed wiring board (approximately 4×5 cm$^2$) that has been photolithographically prepared by standard processes. In the work reported below, the geometry of the test vehicle is defined, the conditions for wetting are described, and the kinetics of wetting are modeled Consider a circular metallization pattern having radius, $r_c$, and let a small volume of solder wet and spread to a radius $r<r_c$ such that capillary equilibrium is obtained at a contact angle, $\Theta_o$. Let the solder volume be increased to a value $V_o$ just large enough to allow the solder to spread to the metallization radius. Any further increase of volume will increase the contact angle to a value $\Theta_+>\Theta_o$, but will not increase the radius since wettable metallization extends only as far as $r_c$. In this quadrajunction configuration, there exists an excess pressure which would drive flow of solder should more metallization be made available. Consider additional metallization in the form of a very slender rectangular strip of width $\delta<r_c$ connected to the circular piece as illustrated in FIG. 1. The excess pressure will tend to move solder onto the strip for certain values of the ratio δ to $r_c$. Solder will then flow a distance, x, reducing the pressure over the circular metallization until it equals that above the strip. To simplify the calculation of these conditions, it will be assumed that the configuration geometry is small enough to neglect the effect of gravity on solder shape. Thus, the solder on the circular metallization has a spherical cross section while the solder on the strip is circular. The height of solder on the strip is given by:

$$h_s = \frac{\delta}{2}\left(\frac{1-\cos\Theta_s}{\sin\Theta_s}\right)$$

where $\Theta_s$ is the equilibrium contact angle on the strip. The mean curvature of the solder surface on the strip is:

$$\frac{1}{R_s} = \frac{2\sin\Theta_s}{\delta} \qquad [1]$$

After solder flows onto the strip, a contact angle, $\Theta_c$, is established on the circular metallization and the capillary pressure is given by:

$$P_c = \frac{2\gamma\sin\Theta_c}{r_c}. \qquad [2]$$

In mechanical equilibrium, the capillary pressures, given by eqs. 1 and 2, must be equal which yields the geometric condition for wetting:

$$\frac{\delta}{r_c} = \frac{\sin\Theta_s}{\sin\Theta_c} \qquad [3]$$

If the strip length is sufficiently long, excess pressure will be zero and since $\delta \neq r_c$, equilibrium, according to eq. 3, must involve contact angle hysterisis if the strip and circular metallizations are identical. Contact angle is known to be a function of the wetting velocity and even exhibits a range or band of static values, $2\Delta\Theta$, in mechanical equilibrium. These phenomena are collectively called contact angle hysterisis. Contact angle hysterisis is usually attributed to substrate surface roughness and chemical heterogeneity, common to most real surfaces, and can slow the smooth advance of the wetting front. With eutectic Sn—Pb solder on rolled copper sheet (with mildly activated rosin flux), observed capillary angles range from approximately 10° to 20°. If $\Theta_o$ is defined as the Young contact angle, it will lie at the approximate center of the range of contact angle hysterisis. For an equilibrium capillary configuration, $\Theta_s$ and $\Theta_c$ must be within or define the extremities of the range of stable contact angles, $2\Delta\Theta$. As solder flows onto the strip, it is reasonable to propose that $\Theta_+$ decreases to a contact angle $\Theta_c = \Theta_o + \Delta\Theta$. For a given geometry, eq. 3 then specifies what value $\Theta_s$ must take for equilibrium. For a Young angle of 15° and a hysterisis range of $2\Delta\Theta=10°$, it is clear that for this range of contact angles, $\delta/r_c$ must be greater than approximately 0.5 if flow is to occur onto the strip. Only in this way will the two contact angles be contained by the stable hysterisis band. Note that if $\delta/r_c=0.25$, there exists no combination of $\Theta_s$ and $\Theta_c$ lying within the $2\Delta\Theta$ hysterisis band that satisfy eq. 3. This implies that flow will not occur onto a strip having this ratio.

The pressure drop along the strip is taken to be $\Delta P = P_c - P_s$ and the kinetics of Poiseuille flow are:

$$\frac{dx}{dt} = \frac{A_s B}{x}\left(\frac{\sin\Theta}{r_c} - \frac{\sin\Theta_s}{\delta}\right) \qquad [4]$$

where, x is the distance solder has flowed onto the strip, t is time measured from the commencement of flow onto the strip, $\theta$ is the temporal contact angle on the circle, and $A_s$ is the cross sectional area of solder on the strip given by:

$$A_s = \frac{1}{8}\left(\frac{\delta}{\sin\Theta_s}\right)^2 (2\Theta_s - \sin 2\Theta_s) \qquad [5]$$

and $$B = \frac{\gamma}{16\pi\eta},$$

where $\gamma$ is the surface tension of the liquid and $\eta$ is the liquid viscosity.

Four (each) measurements of the contact angle on the strip of three solder-tested TVs to characterize their contact angles, $\Theta_s$, were made. The overall average contact angle was 15.6 degrees while the standard deviation was 4.4 degrees. The average contact angle, during flow, was constant relative to that on the circular metallization which decreased in time as flow commenced down the strip. The solder volume, $V_o$, is given by:

$$V_o = \frac{\pi}{6} h(x)(3r_c^2 + h^2(x)) + A_s x \qquad [6]$$

where h(x) is the height of the solder on the circle given by:

$$h(x) = r_c\left(\frac{1-\cos\Theta}{\sin\Theta}\right) \qquad [7]$$

The solder mass (10.1 mg) was kept constant during the experiments and was converted to volume with use of the density (7.91 g/cm$^3$) given by Poirier (D. R. Poirier, *Met. Trans.* A, 1988, vol. 19A, pp. 2349–2354). As a result of reaction with the TV metallization, the volume of solder changes slightly during flow. A simple calculation shows that this volume change is very small so it was assumed that the volume of solder remained constant and equal to its initial value. For any x, eqs. 6 and 7 can be solved for $\Theta$ and substituted into eq. 4 and the resulting differential equation can be solved for x versus flow time. The parameters used for these solutions are: $\delta=0.076$ cm; $r_c=0.102$ cm; $\Theta_s=15.6$ degrees; $\rho=7.91$ g/cm$^3$; and m=10.1 mg.

Figure 10:
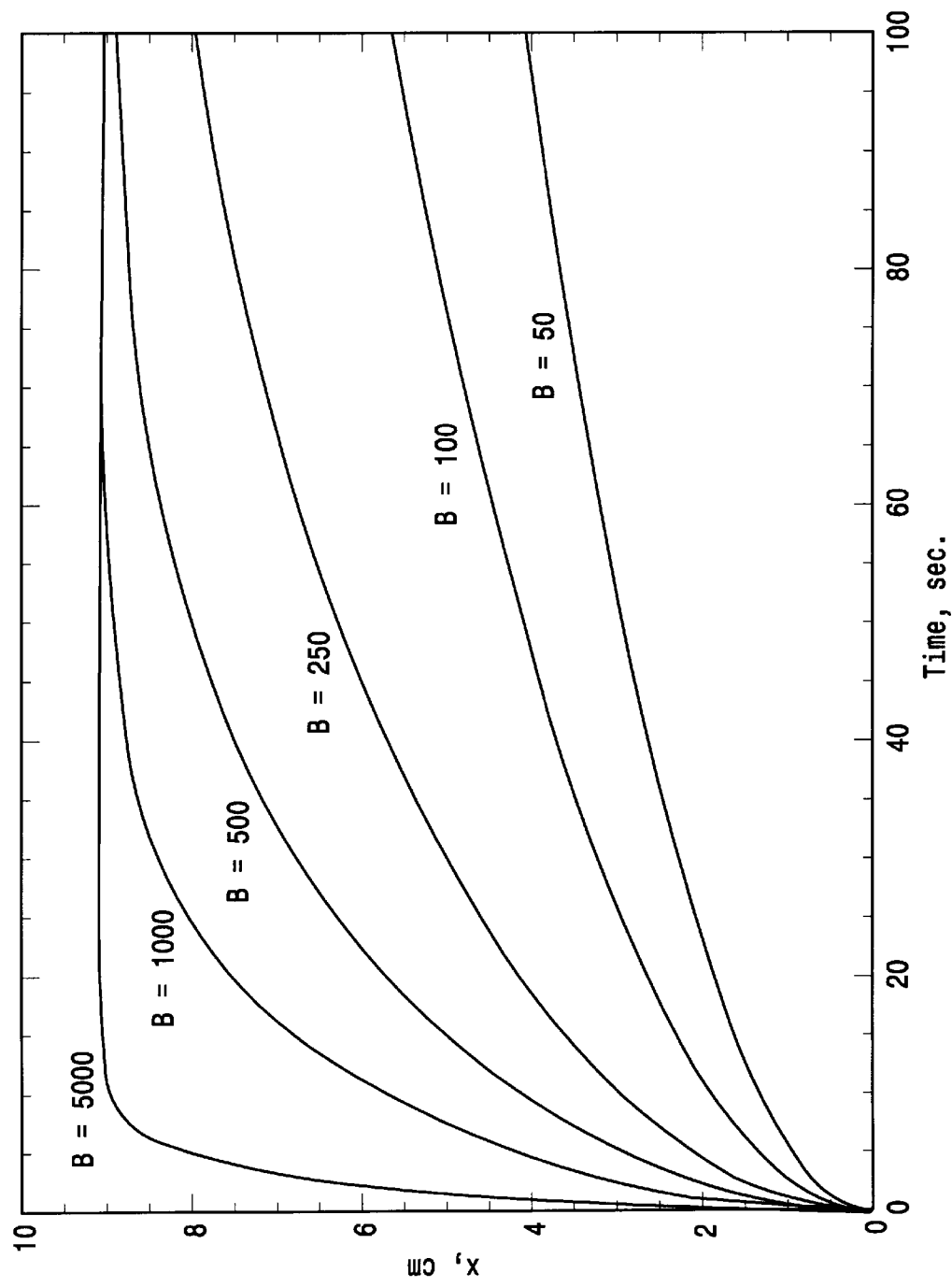
FIG. 10 is a series of graphs of flow distance versus time for several different values for the kinetics parameter, B.
Figure 11:
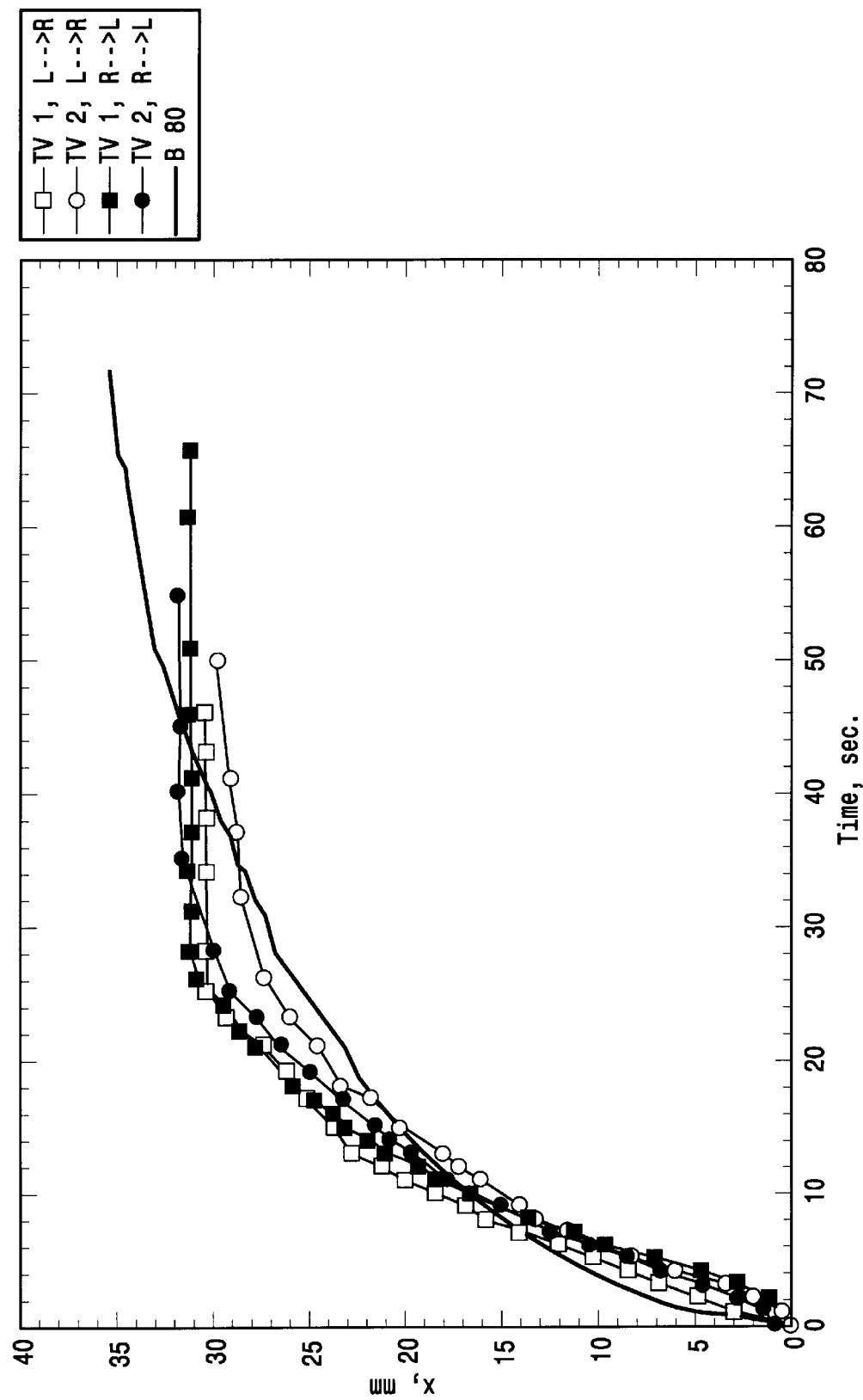
FIG. 11 is a series of graphs comparing experimental and modelled flow rates of solder on the lines.

The appropriate root to the volume constraint (eq. 6) was numerically calculated and used in the simultaneous solution of the non-linear system of eqs. 4–7. Solutions to these equations are shown in FIG. 10. To obtain these solutions several B values were chosen arbitrarily. Depending on the chosen B values, the solutions have parabolic character for the smaller B's while for larger B's they exhibit rapid wetting rates and a pronounced knee. In practice, the 0.076 cm line width (pad radius=0.102 cm) gave the most consistent results. Two of the TVs displayed flow velocities of about 0.15 cm/sec and wetted lengths of about 3.0 cm. A reasonable fit to the kinetics model gave B=80. These results are shown in FIG. 11. Two other TVs gave less consistent results at about 0.075 cm/sec, wetted lengths of about 2.5 cm, and a curve fit to B=40. The inconsistencies are attributed to variations in the fabrication of the TVs.

These flow kinetics were derived in the manner of Poiseuille by equating a viscous dissipation to the driving force for wetting. This yielded an equation for the rate of spreading that could be solved by assuming that the spreading solder droplet was spherical and that volume is conserved. The numerical solutions seemed to "fit" the data for the B values of 80 and 40 above. Assuming a surface energy for liquid solder of 400 mJ/m$^2$ and a bulk viscosity of 0.375 Pa s give a $\gamma/\eta$ ratio of 10700 cm/s and a calculated B of 212 cm/s. It has been shown elsewhere that capillary flow models based on Poiseuille kinetics significantly overestimate the rate of spreading of droplets on flat substrates. This discrepancy is conjectured to arise from a difference between bulk fluid viscosity, as used above, and the effective viscosity at the three phase line where additional energy dissipation is caused by contact and flow against the substrate surface. If the effective viscosity is only a factor of 4 larger than that for the bulk value, very good agreement is obtained between the calculated B and the "fitted" value.

We claim:

1. A system to analyze solderability of printed wiring boards comprising:
    a plurality of lollipop-shaped metallizations each having a circular pad of radius r and a linear strip feature of width d extending therefrom formed on a printed wiring board substrate with at least one such metallization having a different ratio of d:r than another of such metallizations, an amount of solder on at least some of the pads of the metallizations sufficient to form a droplet of liquid solder on the pad whose contact angle is greater than the equilibrium contact angle of the solder, means to heat the solder on the pads to a liquid state, and means to measure a flow characteristic of the liquid solder on the linear feature.

2. The system of claim 1 wherein the flow characteristic is the speed at which the solder flows onto the linear feature.

3. The system of claim 1 wherein the flow characteristic is the terminal length of the solder flow onto the linear feature.

4. The system of claim 1 wherein the flow characteristic is the lack of flow onto the linear feature.

5. The system of claim 1 further comprising means to correlate the flow characteristic to the ratio of d:r.

6. The system of claim 5 wherein the flow characteristic is the speed at which the solder flows onto the linear feature.

7. The system of claim 5 wherein the flow characteristic is the terminal length of the solder flow onto the linear feature.

8. The system of claim 5 wherein the flow characteristic is the lack of flow onto the linear feature.

9. The system of claim 1 further comprising means to correlate the flow characteristic to a surface condition of the metallization.

10. The system of claim 9 wherein the surface condition is contamination.

11. The system of claim 9 wherein the surface condition is roughness.

12. The system of claim 9 wherein the surface condition is oxidation.

13. A method to analyze solderability of printed wiring boards comprising:

placing drops of solder onto a plurality of lollipop-shaped metallizations each having a circular solder pad of radius r onto which the solder is placed and a linear conductor feature of width d extending therefrom, the metallizations being formed on a printed wiring board substrate with at least one such metallization having a different ratio of r:d than another of such metallizations, wherein the amount of solder in a drop is sufficient to form a droplet of liquid solder on the pad whose contact angle is greater than the equilibrium contact angle of the solder, heating the solder on the pads to a liquid state, and measuring a flow characteristic of the solder on the linear feature.

14. The method of claim 13 further comprising the step of correlating the measurement of the flow characteristic of the solder to the ratio of d:r on the metallization.

15. The method of claim 13 further comprising the step of correlating the measurement of the flow characteristic of the solder to a surface condition of the metallization.

16. The method of claim 15 wherein the surface condition is contamination.

17. The method of claim 15 wherein the surface condition is oxidation.

18. The method of claim 15 wherein the surface condition is roughness.

* * * * *